United States Patent [19]
Takazoe et al.

[11] Patent Number: 4,556,429
[45] Date of Patent: Dec. 3, 1985

[54] LOW-CARIOGENIC SWEETNERS

[75] Inventors: Ichiro Takazoe; Kosei Ohta, both of Tokyo; Junichi Shimizu, Yokohama; Kazumasa Suzuki, Ayase; Tatsuya Iwakura, Yokohama; Yoshikazu Nakajima, Yamato, all of Japan

[73] Assignee: Mitsui Sugar Co., Ltd., Tokyo, Japan

[21] Appl. No.: 513,947

[22] Filed: Jul. 14, 1983

Related U.S. Application Data

[63] Continuation of Ser. No. 313,679, Oct. 21, 1981, abandoned.

[30] Foreign Application Priority Data

Oct. 23, 1980 [JP]   Japan ................................ 55-147553

[51] Int. Cl.$^4$ ......................... C13F 3/00; C13K 13/00
[52] U.S. Cl. ....................................... 127/30; 426/658
[58] Field of Search ................... 127/30; 426/658, 650; 424/180; 435/100, 97

[56] References Cited

U.S. PATENT DOCUMENTS 3,836,396  9/1974  McNamara et al. .................. 127/30
3,894,146  7/1975  Tsuyama ......................... 426/658 X
3,912,804  10/1975  Schiweck ........................ 424/180 X

FOREIGN PATENT DOCUMENTS 2344252  6/1973  Fed. Rep. of Germany .
2066639  7/1981  United Kingdom .
2066640  7/1981  United Kingdom .

OTHER PUBLICATIONS

Mitsui; Chem. Abstracts 96:50701g, (9–1981).
Crueger; Chem. Abstracts 90:184932t, (3–1979).
Crueger; Chem. Abstracts 91:156068t, (8–1979).

Primary Examiner—Kenneth M. Schor
Attorney, Agent, or Firm—Kane, Dalsimer, Kane, Sullivan and Kurucz

[57] ABSTRACT

The sweetner prepared by adding palatinose to sucrose is a low-cariogenic since palatinose is not only low cariogenic in itself, but also inhibits the formation of insoluble glucan from sucrose in an oral cavity.

Since the sweetner is almost same as sucrose in quality of sweetness, dissolvability in a mouth, palatability, etc., and further is low-cariogenic when it is used in foods, it is suitable as sweetner. In addition, since the sweetner is usually crystalline or powdery, it is easy to handle.

1 Claim, No Drawings

LOW-CARIOGENIC SWEETNERS

CROSS-REFERENCE TO RELATED APPLICATION

This application is a continuation of U.S. application Ser. No. 313,679, filed Oct. 21, 1981, and now abandoned.

FIELD OF THE INVENTION

This invention relates to a low-cariogenic sweetner and more particularly it relates to a low-cariogenic sweetner comprising sucrose and palatinose.

BACKGROUND OF THE INVENTION

Sucross forms a plaque mainly composed of insoluble glucan on the surfaces of teeth in an oral cavity by the action of Streptococcus mutans (hereinafter, is referred to as S. mutans) which is a cariogenic microbe and then dental caries are produced by the action of acids formed heavily in the plaque.

With the progress of investigations on plaques, it has recently been found that S. mutans be a most principal microbe for causing enamel dental caries. This microbe has a transferase of glucose, which is called "glucosyl-transferase", by the action of which glucose of sucrose is cut from fructose and more than scores of thousands of glucoses are bonded with each other to form a polyglucan. Among these polyglucans, the polyglucan which takes part in the occurrence of dental caries is a water-insoluble polyglucan having an $\alpha$-1,6 bond and an $\alpha$-1,3 bond and hence the polyglucan is called "insoluble glucan". The insoluble glucan is sticky and accumulates the cells of S. mutans on the surfaces of teeth to form cariogenic plaque. If fermentable sugars come into contact with the plaque, they are quickly decomposed into acids to reduce the pH in the plaque below the enamel delimable pH. Furthermore, the plaque containing the insoluble glucan intercepts the buffering, neutralizing, and cleaning actions of salvia, etc. As described above, the formation of the insoluble glucan is a most serious factor for the cariogenic activity of S. mutans. (See, Tadashi Ikeda; "Shikai Tenbo", 49, 684 (1977), R. J. Gibbons and R. J. Fitzgerald; "J. Bacteriol.", 98, 341–346 (1969), T. Ikeda; "Archs oral Biol.", 18, 555 (1973), and I. L. Skklair; "Archs oral Biol.", 19, 199 (1974)).

That is, it is considered that dental caries occur only by the existence of a plaque and also sucrose is a highest-cariogenic material. However, sucrose is an easy-digestible source of calories as well as is an indispensable food for providing abundance and tastefulness to a dietary life. Therefore, it has keenly been desired to prevent the occurrence of the cariogenic action of sucrose, which is the defect of sucrose, but it has not yet been successful to meet the desirement.

Palatinose is a disacharide having the following structural formula and the crystal thereof has 1 mole of water of crystallization. Palatinose has a specific rotation $[\alpha]_D^{20}$ of 97.2 (C=1), a melting point of 122°–123° C., a reducing power of 52% of that of glucose, a solubility in water of 46 g/100 g-solution at 40° C. a viscosity of about 90% of that of sucrose and a sweetness of about 42% of that of sucrose and is used as an easy-digestible source of calorie as sucrose but it has never been reported that palatinose is produced as a sweetner.

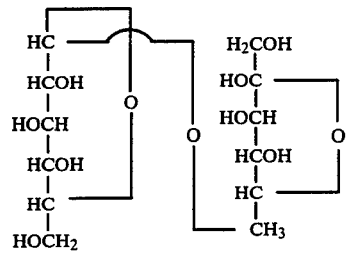

SUMMARY OF THE INVENTION

As the result of various investigations for controlling the cariogenic action of sucrose, the inventors have discovered that, although the foregoing palatinose itself is a low-cariogenic material, when palatinose is added to sucrose, the formation of insoluble glucan from sucrose can be prevented and the cariogenic action of sucrose can be controlled, and the present invention has been attained on the basis of the above discovery.

That is, the invention provides a low-carogenic sweetner comprising sucrose and palatinose.

DETAILED DESCRIPTION OF THE INVENTION

The inventors investigated the action of S. mutans, which is considered to be a cariogenic microbe, on palatinose by performing various experiments.

First, an incubation test was performed for confirming whether or not S. mutans ferments palatinose and it was confirmed that S. mutans showed no fermenting property for palatinose.

Then, a Streptococcus mutans 6715 strain was cultivated in a TTY culture medium (containing 15 g of trypticase, 4 g of tryptose, 4 g of yeast extract, 2 g of $K_2HPO_4$, 2 g of $Na_2CO_3$, 2 g of NaCl, 5 g of $KH_2PO_4$, and 2.5 g/liter of glucose), the cultivated broth was subjected to a centrifugal separation to recover cells obtained, which was washed with a physiological saline solution, and an experiment about acid production was performed using the cell thus obtained. Apart from this, the cell was incubated in a 0.05M potassium phosphate buffer containing 1% each sugar as shown in Table 1 at a cell concentration of 25% by volume and at a temperature of 37° C., and the pH of the system was measured with the passage of time. Furthermore, an experiment was performed for titrating produced lactic acid by 0.01N NaOH with the passage of time by means of a pH automatic titration apparatus using a Streptococcus mutans JC-2 strain. The results showed that no acid was produced in the case of using palatinose.

In the foregoing experiments, S. mutans purely separated was used and when palatinose or other sugar as shown in Table 1 was added to a suspension of plaque at a concentration of 1%, an incubation was aerobically carried out for one hour at 37° C., the reaction was stopped by the additon of metaphosphoric acid, and after recovering the product by a Centrifugal separation, L(+) lactic acid in the supernatant liquid was determined by an enzyme method, it was confirmed that the formation of lactic acid from palatinose was very less as shown in Table 1.

TABLE 1

| | Lactic acid forming rate (μmoles/ml./hr.) | | | |
|---|---|---|---|---|
| Plaque no. | Sucrose | Glucose | Palatinose | No sugar |
| 1 | 0.578 | 0.482 | 0.029 | 0 |
| 2 | 0.573 | 0.658 | 0.011 | 0 |
| 3 | 0.605 | 0.658 | 0 | 0 |

Furthermore, a test was performed for confirming whether or not *S. mutans* formed insoluble glucan from palatinose.

The details of the experiment will be described in Experiments 1, 2 and 3 show below and it was advantageously found by the experiments that when an insoluble glucan-forming enzyme obtained from a supernatant liquid recovered from the cultivation broth of *S. mutans* was reacted with palatinose, insoluble glucan was not formed and also when sucrose and palatinose existed together, the formation of insoluble glucan was remarkably prevented by the inhibiting action of palatinose. The above experiment was enzymatically performed since in a reaction system containing cells the separation of insoluble glucan from the cells is difficult and thence the product cannot accurately be determined.

This phenomenon confirmed by the enzyme reaction will as a matter of course occur in an oral cavity of human being. Therefore, it is presumed that when palatinose is eaten at the same time in the case of eating sucrose, the formation of an insoluble glucan from sucrose remaining in the oral cavity by the action of *S. mutans* is controlled by palatinose existing together with sucrose and the formation of plaque which causes dental caries is reduced.

As shown in Experiment 3, in regard to mixtures of sucrose and palatinose capable of giving a same sweetness as sucrose, the formation of insoluble glucan is controlled to about 50% by the mixing ratio of 20 parts of palatinose and 100 parts of sucrose. Therefore, the case of mixing more than 20 parts of palatinose with 200 parts of sucrose is particularly preferred as the low-cariogenic sweetner of this invention.

As described above, it has been confirmed that palatinose itself is a low-cariogenic sugar and when palatinose exists together with sucrose in an oral cavity, palatinose shows such a positive low-cariogenic effect as inhibiting the formation of insoluble glucan from sucrose in the oral cavity. This backs up that the occurrence of dental caries by sucrose can be prevented by palatinose and the sweetner of this invention meets the demand of "the appearance of a nutritious sweetner which causes less decayed teeth, has a good taste, and is easily used together with other preferred properties thereof.

As stated above, the sweetness of palatinose is about 42% of that of sucrose per weight. The sweetness of the sweetner of this invention is about 90% of that of sucrose per weight in the case of 100 parts of sucrose and 20 parts of palatinose, about 85% in the case of 100 parts of sucrose and 35 parts of palatinose, and about 71% in the case of 100 parts of sucrose and 100 parts of palatinose. Also, the quality of sweetness of the sweetners of this invention is almost same as that of sucrose and is preferably. Thus, by adding more than 20 parts of palatinose to 100 parts of sucrose, a sweetner which meets the present tendency that cakes and other foods having reduced sweetness are desired is provided.

In particular, the sweetners of this invention comprising 100 parts of sucrose and 20-35 parts of palatinose are preferred in not only the foregoing low-cariogenic property but also food processing characteristics. That is, when the sweetners of this invention comprising 100 parts of sucrose and 20-35 parts of palatinose are used for cookies, candies, etc., the products having almost same sweetness, dissolvability, tastiness, etc., as those of products prepared using sucrose only. On the other hand, when the proportion of palatinose is over 35 parts to 100 parts of sucrose, the sweetness of the products becomes weak and there is a tendency that the characters of the products such as dissolvability, tastiness, etc., become undesirable as compared to the case of using sucrose only.

Also, when the sweetners of this invention comprising 100 parts of sucrose and 20-35 parts of palatinose are used for high-sugar containing foods such as jam, ice cream, etc., the deposition of the crystals of sugar does not occur, and there is no trouble of reducing the quality of the foods. Moreover, as compared to the foods prepared using sucrose only as the sweetner, the foods prepared using the sweetners of this invention show almost same enhancement of flavor, dissolvability, tastiness, etc. On the other hand, when more than 35 parts of palatinose is used to 100 parts of sucrose, the deposition of the crystals of sugar occurs, the texture of products becomes coarse, and tastiness is reduced.

Therefore, for obtaining preferred foods having a low-cariogenic effect and other same properties as the case of using sucrose only, it is preferred to use a sweetner comprising 100 parts of sucrose and 20-35 parts of palatinose.

Coupling sugar has recently been produced as a low-cariogenic sweetner. Coupling sugar is a millet jelly composed of a mixture of various oligosaccharide and hence it is very difficult to make powders or crystals of it. On the other hand, palatinose used in this invention is a single material, sucrose is converted into palatinose by the action of an enzyme converting sucrose into palatinose, and palatinose formed can be easily recovered from the reaction mixture as the crystals or powder. Also, palatinose itself has a character of greatly controlling or inhibiting the formation of insoluble glucan from sucrose by the action of *S. mutans*. Furthermore, since the low-cariogenic sweetner of this invention prepared by adding palatinose to sucrose can easily provide the crystal or powder thereof, the sweetner of this invention can be handled very easily and hence can be used widely as compared to coupling sugar. Moreover, in regard to the quality of sweetness, coupling sugar has a taste of a millet jelly but the sweetner of this invention comprising sucrose and palatinose has a preferred quality of sweetness very similar to that of sucrose. Thus, the sweetners of this invention are very superior to coupling sugar in the low-cariogenic and economical aspects.

Also, coupling sugar, sucrose, maltose, etc., is easily hydrolyzed in an acid state to form fructose or glucose but palatinose is reluctant to be hydrolyzed as compared with these sugars, which shows that the sweetner of this invention comprising sucrose and palatinose is more stable as compared with above-described conventional sweetners in the case of using for a soft drink, etc., under an acid condition.

The sweetner of this invention is used as the form of a powder, crystal or liquid comprising sucrose and palatinose but can be used as the form of a square sugar of sucrose coated with the crystals of palatinose. Also, it may be used as the form of the crystal of palatinose coated with sucrose.

As applications of the sweetners of this invention, there are candies composed of the masses of fondant-like molasses containing fine crystals of palatinose coated with chocolate containing sucrose; wheat glutens, candies, caramels, etc., prepared using a mixture of sucrose and palatinose as the main raw material; and various kinds of Japanese confectionaries, Western confectionaries, cold confectionaries, soft drinks, luxury drinks, etc., containing sucrose and palatinose as the sweetner.

The following experiments show the fact that when palatinose is added to sucrose according to this invention, the formation of insoluble glucan, which causes dental caries, is remarkably inhibited.

Experiment 1

Tested palatinose: Crystal palatinose having a purity above 99.8% and containing no other sugars.

Procedure: From a supernatant liquid of a cultivated broth prepared by cultivating a Streptococcus mutans 6715 strain in a TTY culture medium was precipitated an insoluble glucan-forming enzyme, glucosyltransferase with a 50%-saturated ammonium solution, the precipitated enzyme was dissolved in a 0.05M potassium phosphate buffer (pH 6.8), and the enzyme thus dissolved was dialyzed into a buffer solution having the same composition as the foregoing buffer. To 0.05M potassium phosphate buffer (pH 6.8) were added 0.1 ml of the crude enzyme solution, 0.01% of merthiolate for preventing microbial infection, and each of the sugars as shown in Table 2 in a final concentration to provide 2 ml of a reaction mixture. After allowing the liquid to react for 17 hours at 37° C., an insoluble glucan thus formed was collected by centrifugal separation, and after washing the glucan, the determination of it was performed. The results are shown in Table 2.

TABLE 2

| Substrate | Formed insoluble glucan | |
|---|---|---|
| | mg | index |
| 2% sucrose | 4.26 | 100 |
| 1% sucrose | 3.45 | 81.0 |
| 1% palatinose | 0 | 0 |
| 1% sucrose + 1% palatinose | 1.14 | 26.8 |

From the results, it has been clarified that when palatinose is added to sucrose, palatinose cannot become a substrate for forming insoluble glucan causing dental caries as well as has an action of inhibiting the formation of insoluble glucan from sucrose.

Experiment 2

For obtaining more detailed knowledge about the action of palatinose for inhibiting the formation of insoluble glucan, it was tested to know the change of the formation amount of insoluble glucan in the case of adding 0, 0.25%, 0.5% or 1.0% palatinose to sucrose in a concentration of 0.25%, 0.5%, 1.0%, 2.0%, or 4.0%. The experimental procedure was same as that in Experiment 1 except that the concentrations of sucrose and palatinose were changed. Thus, the results as shown in Table 3 were obtained about the reaction between the formation amount (the amount (mg) formed in 2 ml of the reaction liquid) and the concentrations of sucrose and palatinose.

TABLE 3

Concentrations of sucrose and palatinose and the formation amount of insoluble glucan

| Concentration of sucrose (%) | Concentration of palatinose (%) | | | |
|---|---|---|---|---|
| | 0 | 0.25 | 0.5 | 1.0 |
| 0.25 | 1.27 | 0.70 | 0.52 | 0.38 |
| 0.5 | 2.25 | 1.38 | 1.18 | 0.70 |
| 1.0 | 4.24 | 1.68 | 1.55 | 0.98 |
| 2.0 | 5.37 | 2.17 | 1.96 | 1.02 |
| 4.0 | 5.62 | 2.56 | 2.05 | 1.23 |

From the data shown in Table 3, it is clear that as the concentration of palatinose is higher, the formation of insoluble glucan from sucrose is more inhibited.

Experiment 3

Based on the fact that palatinose has a sweetness of 42% of that of sucrose, solutions of various mixtures of sucrose and palatinose having a same sweetness as that of a 2% sucrose solution were prepared by calculation and when the same experiment as in Experiment 1 was performed on the formation of insoluble glucan about each case, the results shown in Table 4 were obtained.

TABLE 4

| Mixing ratio A/B × 100 | Formation of insoluble glucan in a same sweetness: | | | |
|---|---|---|---|---|
| | Sugar concentration (%) | | Insoluble glucan | |
| | Sucrose | Palatinose | mg/2 ml. 17 hr. | Index |
| 0 | 2.0 | 0 | 5.25 | 100 |
| 5 | 1.96 | 0.10 | 3.79 | 72 |
| 10 | 1.92 | 0.19 | 3.03 | 58 |
| 20 | 1.85 | 0.37 | 2.16 | 41 |
| 30 | 1.78 | 0.53 | 1.71 | 33 |
| 40 | 1.71 | 0.68 | 1.43 | 27 |
| 50 | 1.65 | 0.83 | 1.22 | 23 |
| 70 | 1.54 | 1.08 | 0.98 | 19 |
| 100 | 1.40 | 1.40 | 0.78 | 15 |

(A): palatinose
(B): sucrose

From the above results, it is understood that when 20 parts of palatinose is mixed with 100 parts of sucrose, the formation of insoluble glucan is about ½ of that in the case of sucrose only and when more than 20 parts of palatinose is added, the effect of inhibiting the formation of insoluble glucan is particularly remarkable.

Then, the production examples of the low-cariogenic sweetner of this invention are described in the following examples together with the properites and uses.

EXAMPLE 1

A low-cariogenic sweetner of this invention was prepared by adding 11.1 parts, 25.0 parts, 30.0 parts, 42.9 parts, 80 parts, or 100 parts of crystal palatinose to 100 parts of crystal sucrose followed by mixing. Then, a 10% aqueous solution of each sweetner was prepared. As comparison solution, an aqueous solution of 7.0%, 7.5%, 8.0%, 8.5%, 9.0%, 9.5%, 10.0% or 10.5% sucrose was prepared, the sucrose solutions having a same sweetness were selected by 15 panelers and at the same time the difference in taste at the same sweetness was evaluated by them. The results are shown in Table 5. The sweetnesses almost coincided with the calculated values from each sweetness of sucrose or palatinose and the taste of the aqueous solutions of the mixtures of sucrose and palatinose was almost same as that of the solutions of sucrose.

TABLE 5

| No. | Mixing ratio of palatinose to 100 parts of sucrose | Sweetness Measured value by functional test | Sweetness Calculated value* | Difference in taste of sweetness compared with sucrose solution |
| --- | --- | --- | --- | --- |
| 1 | 11.1 parts | 93 | 94.2 | no difference |
| 2 | 25.0 parts | 91 | 88.4 | " |
| 3 | 30.0 parts | 87 | 86.6 | " |
| 4 | 42.9 parts | 81 | 82.6 | " |
| 5 | 80.0 parts | 74 | 74.0 | " |
| 6 | 100 parts | 72 | 71.0 | " |

(*): The calculated value when the sweetness of sucrose was defined as 100 and that of palatinose as 42.

EXAMPLE 2

A low-cariogenic sweetner of this invention was prepared by mixing 50 parts of crystal palatinose with 100 parts of crystal sucrose. From the formation of insoluble glucan in a same sweetness shown in Table 4 in Experiment 3, it is clear that the insoluble glucan formation index of the low-cariogenic sweetner of this invention to sucrose having the same sweetness is about 23.

Apart from this, one liter of hot water was added to 12 g of instant coffee and 24 g of instant powdered cream and 340 g of the mixture was mixed with 22.3 g of the foregoing low-cariogenic sweetner of this invention. For comparison, coffee having almost the same sweetness as above was prepared by adding 18 g of crystal sucrose to 340 g of the foregoing mixture. The sweetness and the taste of both coffees were evaluated by 15 panelers.

The results are as follows:

| | | |
| --- | --- | --- |
| Sweetness: | The coffee containing the sweetner of this invention was less sweet. | 2 panelers |
| | No difference between them. | 10 panelers |
| | The coffee containing the sweetner of this invention was more sweet. | 3 panelers |
| Taste: | No difference between them. | 5 panelers |
| | Distinguishable but it was difficult to indicate which was preferable. | 10 panelers |

EXAMPLE 3

A powdered juice containing the low-cariogenic sweetner of this invention (100 parts of sucrose and 42.9 parts of palatinose) and a comparison powdered juice containing sucrose as the sweetner each having the composition as shown in the following table were prepared.

From "the formation of insoluble glucan in a same sweetness" in Table 4 of Experiment 3, it is clear that the insoluble glucan forming index of the low-cariogenic sweetner of this invention to sucrose having the same sweetness is less than 30.

| | Powdered juice containing the sweetner of the invention | Comparison powdered juice |
| --- | --- | --- |
| Powdered mandarin juice | 40 g | 40 g |
| Citric anhydride | 16.2 g | 16.2 g |
| Fumaric acid | 8.1 g | 8.1 g |
| Sodium citrate | 5.5 g | 5.5 g |
| Vitamin C | 3.3 g | 3.3 g |
| Orange powdered perfume | 9.0 g | 9.0 g |
| Palatinose | 319 g | — |
| Sucrose | 743 g | 877 g |
| total | 1144.1 g | 959.1 g |

To 11.4 g of the powdered juice containing the sweetner of this invention or 9.5 g of the comparison powdered juice was added water to form 100 ml of each solution and the sweetness and taste of the solutions were evaluated by 20 panelers and the following results were obtained.

| | | |
| --- | --- | --- |
| Sweetness: | In the powdered juice containing the sweetner of this invention; the sweetness was high | 5 panelers |
| | no difference | 12 panelers |
| | the sweetness was low | 3 panelers |
| Taste: | In the powdered juice containing the sweetner of this invention; the taste was preferred | 3 panelers |
| | no difference or no answer | 16 panelers |
| | the taste was not preferred | 1 paneler |

EXAMPLE 4

Three yolks of eggs and a definite amount of a sugar in Table 6 (i.e., palatinose, sucrose, or a mixture of them) were mixed well in a bowl by means of a stirrer. Furthermore, 240 ml of a milk heated to 60°–70° was added to the mixture, while mixing the resultant mixture by a large wooden spoon, the mixture was softly heated, when the mixture became viscous, heating was stopped and the mixture was cooled. Then, 100 ml of whipped raw cream and a small amount of a vanilla essence were mixed with the resultant mixture.

The raw material of ice cream thus prepared was placed in a vessel for Ice Creamer (made by Oster Co.) to a scale of 400 ml. Ice (about 800 g) and sodium chloride (about 200 g) were placed alternatively around the vessel and the switch of the Ice Creamer was turned on. After 15 minutes, ice cream was prepared and after storing overnight the ice cream in a refrigerator at −20° C., the ice cream was tasted. The results are shown in Table 6.

From the results, it is understood that the samples No. 2, No. 3, and particularly No. 3 containing the low-cariogenic sweetners of this invention are excellent in the points of sweetness, enhancement of flavor, and total preferability.

TABLE 6

| | Sample | | | Tasted results | | | | |
| --- | --- | --- | --- | --- | --- | --- | --- | --- |
| No. | (A) | (B) | (A)/(B) | Sweetness | Palatability | Enhancement of flavor | Total preferability | Note |
| 1 | 90 g | 0 | — | deficiency | feel rough | ++ | + | low-cariogenic sweetner used |
| 2 | 45 g | 45 g | 100/100* | slightly less | almost no feel | ++++ | +++ | low-cariogenic sweetner of this |

TABLE 6-continued

| | Sample | | | Tasted results | | | | |
|---|---|---|---|---|---|---|---|---|
| No. | (A) | (B) | (A)/(B) | Sweetness | Palatability | Enhancement of flavor | Total preferability | Note |
| 3 | 22.8 g | 67.2 g | 33.9/100* | good | rough very smooth | +++++ | +++++ | invention used low-cariogenic sweetner of this invention used |
| 4 | 0 | 90 g | — | good | smooth | +++ | +++ | conventional standard ice cream, high-cariogenic sweetner (sucrose) used. |

(A): palatinose,
(B): sucrose,
(*): by weight part

What is claimed is:

1. A low-cariogenic sweetner which consists of a mixture of sucrose and palatinose wherein the proportion of palatinose is from 20 to 35 parts by weight per 100 parts by weight of sucrose.

* * * * *

UNITED STATES PATENT AND TRADEMARK OFFICE
CERTIFICATE OF CORRECTION

PATENT NO. : 4,556,429

DATED : December 3, 1985

INVENTOR(S) : Ichiro Takazoe et al

It is certified that error appears in the above-identified patent and that said Letters Patent is hereby corrected as shown below:

Col. 2, line 11 in the diagram -"$CH_3$" in right hand column should read -- $CH_2$ --

Col. 3, line 38; - "200 parts " should read -- 100 parts --

Signed and Sealed this

Twenty-fifth Day of March 1986

[SEAL]

Attest:

DONALD J. QUIGG

Attesting Officer

Commissioner of Patents and Trademarks